(12) United States Patent
Hibino et al.

(10) Patent No.: US 6,817,224 B2
(45) Date of Patent: Nov. 16, 2004

(54) STRUCTURE OF GAS SENSOR

(75) Inventors: Hideki Hibino, Kariya (JP); Toshimi Miyamoto, Okazaki (JP)

(73) Assignee: Denso Corporation (JP)

( * ) Notice: Subject to any disclaimer, the term of this patent is extended or adjusted under 35 U.S.C. 154(b) by 509 days.

(21) Appl. No.: 09/810,175

(22) Filed: Mar. 19, 2001

(65) Prior Publication Data

US 2001/0022104 A1 Sep. 20, 2001

(30) Foreign Application Priority Data

Mar. 17, 2000 (JP) ........................................ 2000-075906
Mar. 2, 2001 (JP) ........................................ 2001-059002

(51) Int. Cl.[7] ...................... G01N 33/497; G01M 19/00
(52) U.S. Cl. ...................................... 73/23.31; 73/118.1
(58) Field of Search ............................... 73/23.31, 116, 73/118.1, 23.32, 118.2

(56) References Cited

U.S. PATENT DOCUMENTS

| | | | |
|---|---|---|---|
| 6,222,372 B1 * | 4/2001 | Fukaya et al. | 324/464 |
| 6,296,749 B1 * | 10/2001 | Balch et al. | 204/452 |
| 6,679,099 B2 * | 1/2004 | Fujita et al. | 73/23.2 |
| 2002/0138967 A1 * | 10/2002 | Hattori et al. | 29/592 |
| 2003/0150254 A1 * | 8/2003 | Fujita et al. | 73/23.2 |
| 2004/0011646 A1 * | 1/2004 | Nakagawa et al. | 204/428 |

FOREIGN PATENT DOCUMENTS

| | | | | |
|---|---|---|---|---|
| EP | 0899562 A2 | 3/1999 | | |
| EP | 0918215 A2 | 5/1999 | | |
| EP | 918215 A2 * | 5/1999 | ......... | G01N/27/407 |
| JP | 11-72471 | 3/1999 | | |
| JP | 2000-121598 | 4/2000 | | |

* cited by examiner

*Primary Examiner*—Edward Lefkowitz
*Assistant Examiner*—Maurice Stevens
(74) *Attorney, Agent, or Firm*—Nixon & Vanderhye PC

(57) ABSTRACT

An improved structure of a gas sensor is provided which may be employed in an oxygen measuring device of an air-fuel ratio control system measuring an oxygen content in exhaust gasses of an internal combustion engine of automotive vehicles. The gas sensor includes a sensing unit which is disposed in a housing and has defined in an end portion thereof a reference gas chamber to be filed with a reference gas used in determining a given gas component content in gasses, a metallic cover installed on the housing to cover the other end portion of the sensing unit; and a cylindrical insulation porcelain disposed in the metallic cover. The insulation porcelain has a groove formed on an outer peripheral wall thereof to define a portion of a reference gas passage communicating between an air inlet formed in the metallic cover and the reference gas chamber. The outer peripheral wall is substantially circular in cross section for avoiding the deformation of the insulation porcelain arising in compressing a material of the insulation porcelain such as ceramic powder during a manufacturing process.

10 Claims, 17 Drawing Sheets

FIG. 16
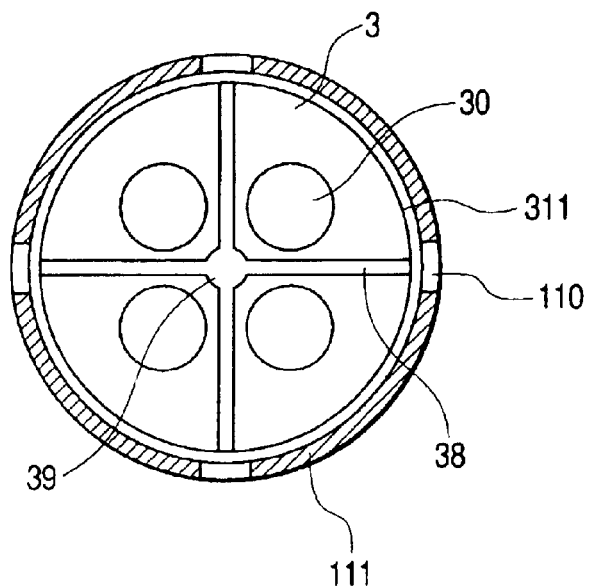
FIG. 17(a)     FIG. 17(b)     FIG. 17(c)
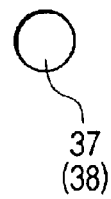
37
(38)
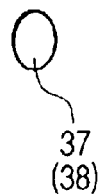
37
(38)
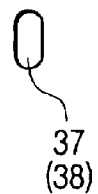
37
(38)

STRUCTURE OF GAS SENSOR

BACKGROUND OF THE INVENTION

1. Technical Field of the Invention

The present invention relates generally to an improvement on a gas sensor which may be employed in an oxygen measuring device of an air-fuel ratio control system measuring an oxygen content in exhaust gasses of an internal combustion engine of automotive vehicles.

2. Background Art

For burning control of fuel in internal combustion engines, modem automotive vehicles use a gas sensor, e.g., as an oxygen sensor which is installed in an exhaust system to measure the concentration of oxygen in exhaust gasses.

European Patent Application EP 0918215 A2 teaches an oxygen sensor designed to define an air gap between an insulation porcelain and a metallic cover which is large enough for admitting air used as a reference gas in determining the concentration of oxygen. FIG. 21(a) illustrates the insulation porcelain disclosed in this application. The insulation porcelain 9 consists of a large-diameter portion 92 and a small-diameter portion 91. The small-diameter portion 91 is of a rectangular shape and has formed therein through holes 30 within which lead lines are held. The insulation porcelain 9 is fitted within a metallic cover (not shown) to define the air gap between an inner wall of the metallic cover and the small-diameter portion 91.

The formation of the insulation porcelain 9, however, experiences, as shown in FIG. 21(b), the deformation of the small-diameter portion 91 in compressing the ceramic powder because the interval O between an outer wall 911 of the small-diameter portion 91 and an outer wall 921 of the large-diameter portion 92 varies in a circumferential direction of the insulation porcelain 9, thus resulting in a decreased strength of the insulation porcelain 9. This problem is common to gas sensors of the type having a reference gas chamber admitting a reference gas used in determining the concentration of a specific gas.

SUMMARY OF THE INVENTION

It is therefore a principal object of the invention to avoid the disadvantages of the prior art.

It is another object of the invention to provide an improved structure of a gas sensor capable of admitting a sufficient amount of a reference gas into a reference chamber without scarifying the strength of an insulation porcelain.

According to one aspect of the invention, there is provided an improved structure of a gas sensor designed to measure a given component content in a gas. The gas sensor comprises: (a) a housing; (b) a sensing unit having a length disposed in the housing, the sensing unit having defined in a first end portion thereof a reference gas chamber to be filed with a reference gas used in providing a sensor signal through a lead which is employed in determining the given gas component content in the gas; (c) a first metallic cover installed on the housing to cover a second end portion of the sensing unit; (d) a second metallic cover installed on a periphery of the first metallic cover; (e) a first vent formed in the first metallic cover; (f) a second vent formed in the second metallic cover which communicates with the firs vent to admit the reference gas into the reference gas chamber through a reference gas passage; and (g) an insulating member disposed in the first metallic cover, having formed therein a hole through which the lead passes to connect with the sensing unit, the insulating member being made of a cylindrical porcelain having an outer peripheral wall which is substantially circular in cross section and which defines the reference gas passage.

In the preferred mode of the invention, the insulating member has a first end surface and a second end surface opposed to the first end surface in a longitudinal direction of the gas sensor parallel to the length of the sensing unit. The insulating member has a through hole extending in a direction of the first end surface to the second end surface to define a portion of the reference gas passage.

The insulating member is arranged in alignment with the sensor unit and has a groove formed in the outer peripheral wall which extends from the first vent to the first end surface to define a portion of the reference gas passage.

The insulating member has a small-diameter portion formed closer to the first end surface and a large-diameter portion continuing from the small-diameter portion. If a length of the small-diameter portion in a direction is defined as L1, a distance L2 between the large-diameter portion and an upstream end of the groove facing the first vent lies within a range of L1/5 to L1/2.

The first vent has a diameter R in the longitudinal direction of the gas sensor. The distance between a point on a periphery of the first vent closest to the second end surface of the insulating member and an upstream end of the groove facing the first vent is greater than or equal to R/3.

The insulating member may alternatively have a groove formed in the outer peripheral wall which extends from the first vent to the second end surface to define a portion of the reference gas passage.

If a plane tangent to a periphery of the insulating member is defines as P, a plane passing through the deepest point of the groove in parallel to the plane P is defined as P1, and a plane passing in parallel to the plane P through the center of the through hole formed in the insulating member is defined as P2, a distance S1 between the planes P and P1 is smaller than or equal to a distance S2 between the planes P and P2.

If a width of the reference gas passages defined on the outer peripheral wall of the insulating member is defined as H1, and a diameter of the insulating member is defined as H2, they are so selected as to meet a condition of $H1 \leq H2/2^{1/2}$.

The insulating member may alternatively have formed therein a plurality of lead holes through which leads pass to connect with the sensing unit. The reference gas passage may be defined at a location where a line passing through a center of the insulating member between adjacent two of the lead holes intersects the outer peripheral wall of the insulating member.

The reference gas passage may alternatively be defined by a hole formed in the insulating member which extends from a portion of the outer peripheral wall of the insulating member facing the first vent and communicates with the hole through which the lead passes.

The insulating member may have formed therein a lateral hole extending between the lead holes in communication with the through hole extending in the direction of the first end surface to the second end surface of the insulating member to define the reference gas passage.

The reference gas passage may alternatively be defined by a through hole formed in the insulating member which extends from a portion of the outer peripheral wall facing the first vent to the chamber through the small-diameter portion and the large-diameter portion.

The reference gas passage may alternatively be defined by an inner wall of the first metallic cover and a surface of the outer peripheral wall of the insulating member tapering off to the first end surface.

The reference gas passage may alternatively be defined by an inner wall of the first metallic cover and a first and a second annular step formed on the outer peripheral wall of the insulating member. The first annular step is smaller in diameter than the second step.

BRIEF DESPCRIPTION OF THE DRAWINGS

The present invention will be understood more fully from the detailed description given hereinbelow and from the accompanying drawings of the preferred embodiments of the invention, which, however, should not be taken to limit the invention to the specific embodiments but are for the purpose of explanation and understanding only.

In the drawings:

FIG. 16 shows a modification of the fourth embodiment in FIGS. 13(a) and 13(b);

Figure 18A:
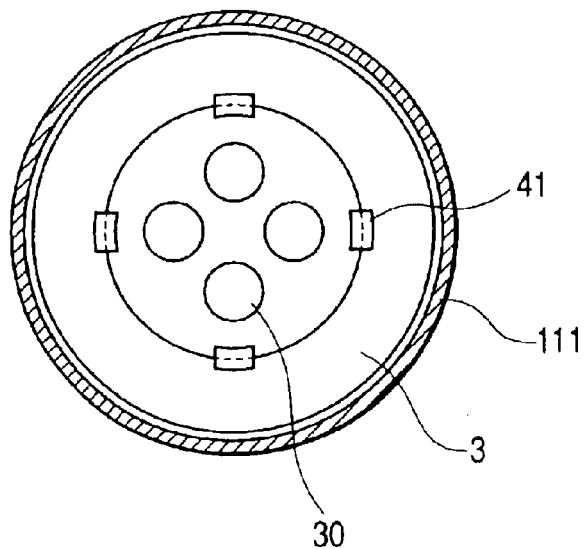
Figure 18B:
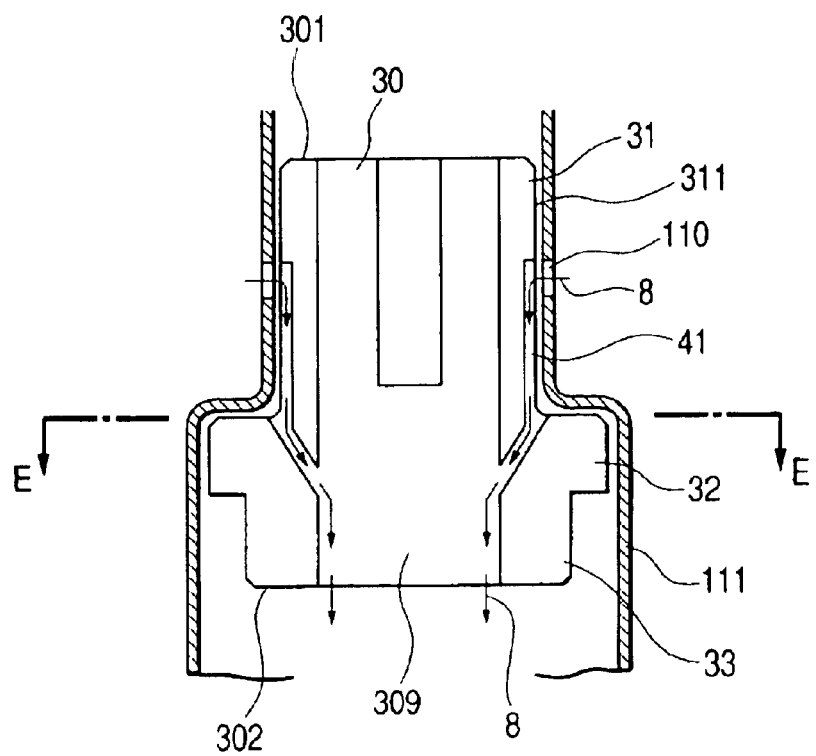
Figure 19A:
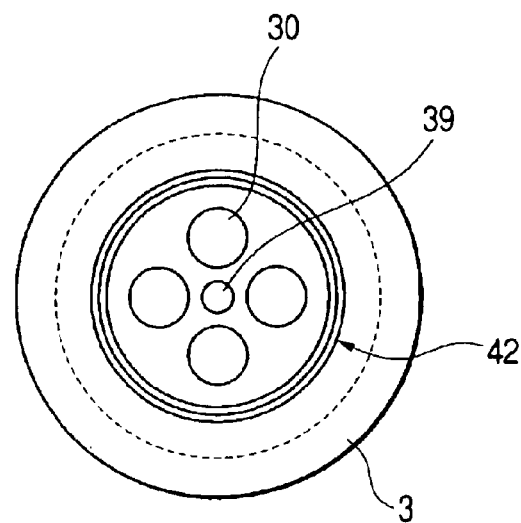
Figure 19B:
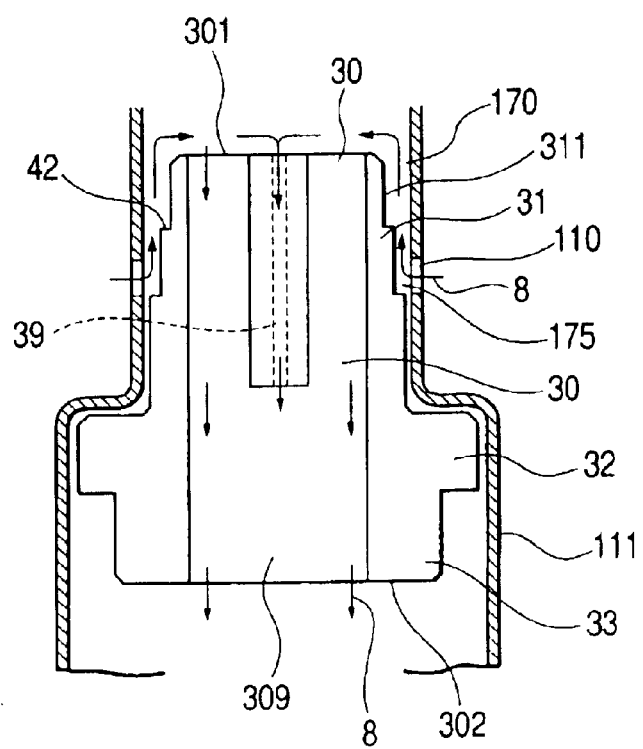
Figure 20:
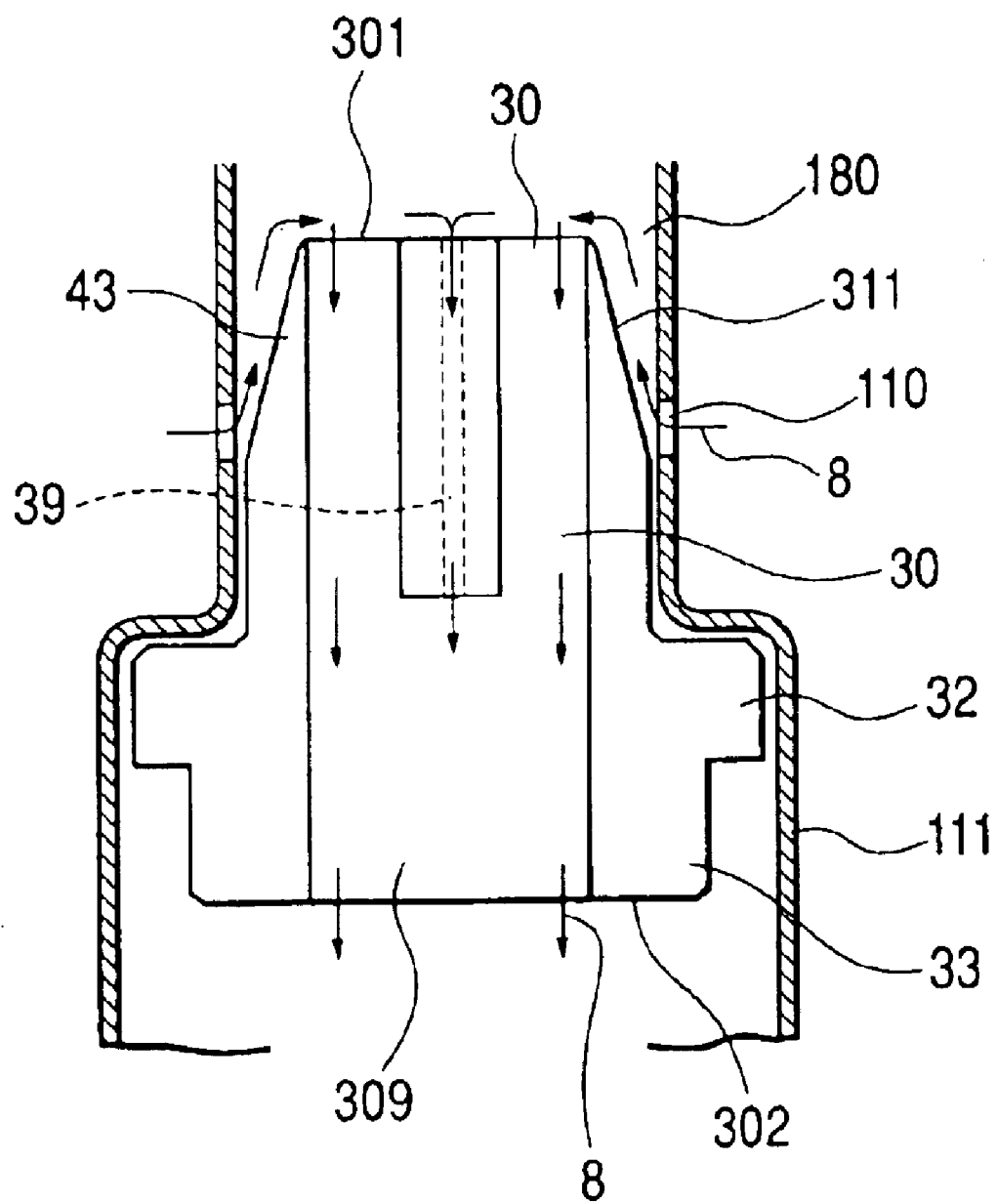
Figure 21A:
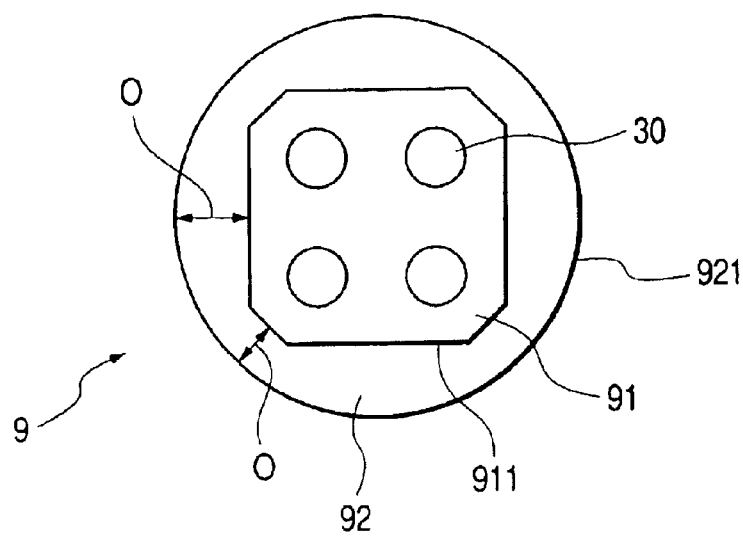
Figure 21B:
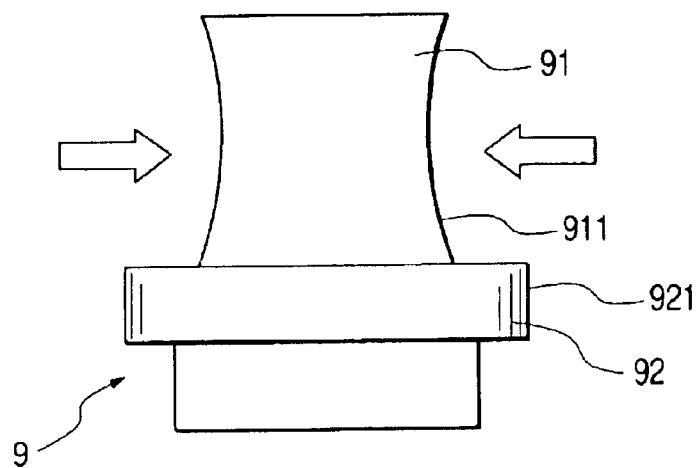

FIGS. 17(a), 17(b), and 17(c) show modifications of reference gas passages, as shown in FIGS. 14(a), 14(b), 15(a), 15(b), and 16;

FIG. 18(a) is a horizontal sectional view taken along the line E—E in FIG. 18(b);

FIG. 18(b) is a longitudinal sectional view which shows reference gas passages defined in an insulating holder of the sixth embodiment of the invention;

FIGS. 19(a) and 19(b) show an insulating holder according to the seventh embodiment of the invention;

FIG. 20 shows an insulating holder according to the eighth embodiment of the invention; and FIG. 21(a) is a plan view which shows a conventional insulating holder installed in an oxygen sensor; and FIG. 21(b) is a side view which shows the insulating holder of FIG. 21(a) which is deformed during a production process.

DESCRIPTION OF THE PREFERRED EMBODIMENTS

Figure 1:
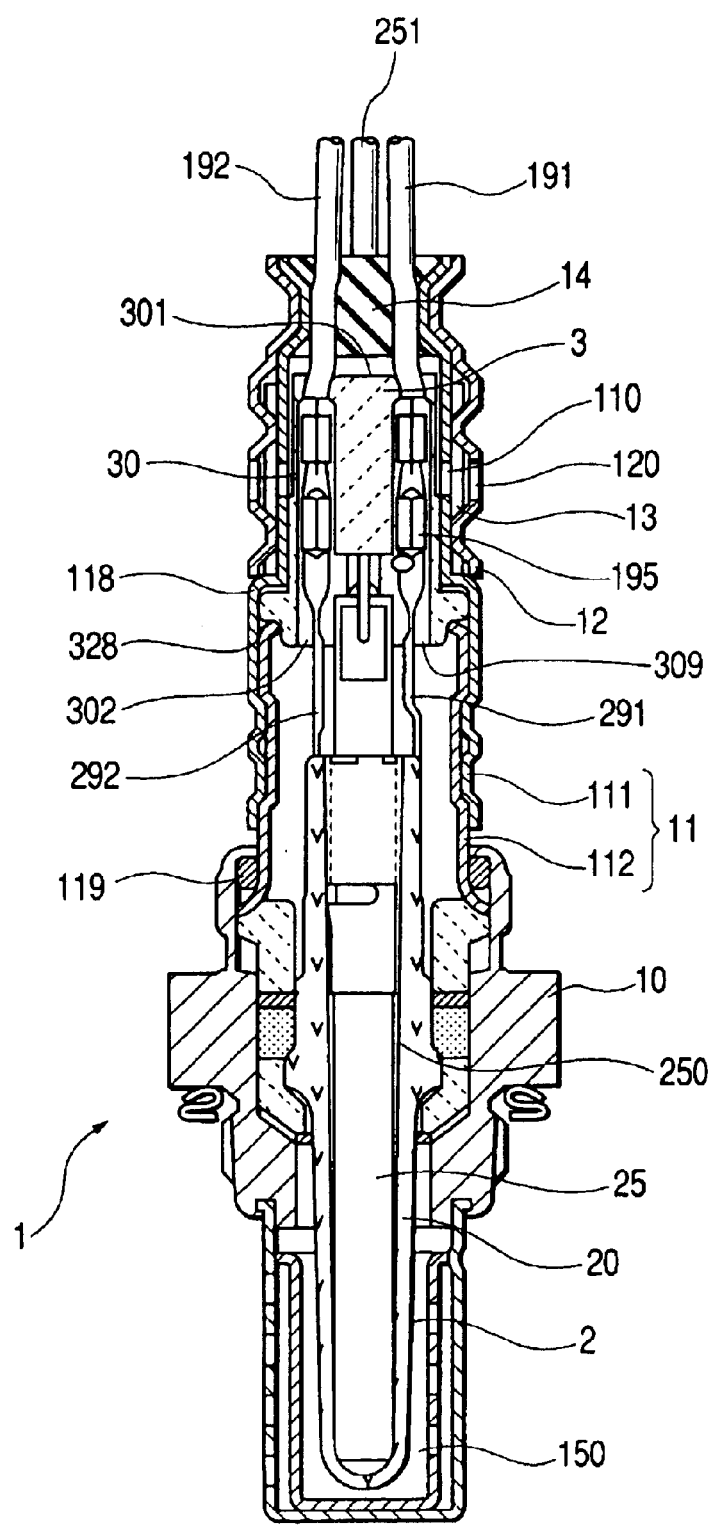
FIG. 1 is a longitudinal sectional view which shows an oxygen sensor equipped with an insulating holder according to the first embodiment of the invention.

Referring to the drawings, wherein like reference numbers refer to like parts in several views, particularly to FIG. 1, there is shown an oxygen sensor 1 according to the first embodiment of the invention which may be employed in an air-fuel ratio control system for automotive vehicles. Note that the present invention is not limited to an oxygen sensor and may alternatively used with a variety of gas sensors such as HC, CO, and NOx sensors.

The oxygen sensor 1 generally includes, a housing 10, a sensing unit 2, and signal leads 291 and 292 connected to the sensing unit 2. The signal leads 291 and 292 provide sensor signals to an external device which are used, as will be described later in detail, in determining the concentration of oxygen contained in a gas. The sensing unit 2 has formed therein a reference gas chamber 250 into which a reference gas (i.e., air) is admitted for use in providing the sensor signals through the signal leads 291 and 292. This technique is well known in the art, and explanation thereof in detail will be omitted here. For instance, U.S. application Ser. No. 09/196,693, filed on Nov. 20, 1998, assigned to the same assignee as that of this application teaches a gas measuring method in this type of gas sensor, and disclosure of which is incorporated herein by reference.

The oxygen sensor 1 also includes a first metallic cover 11 and a second metallic cover 12. The first metallic cover 11 covers a base portion of the sensing unit 2 and is fitted in an end of the housing 10. The second metallic cover 12 is disposed around an upper portion of the first metallic cover 11, as viewed in the drawing. The first and second metallic covers 11 and 12 have formed therein first and second air vents 110 and 120 in alignment with each other for admitting the reference gas into the reference gas chamber 250.

Figure 2:
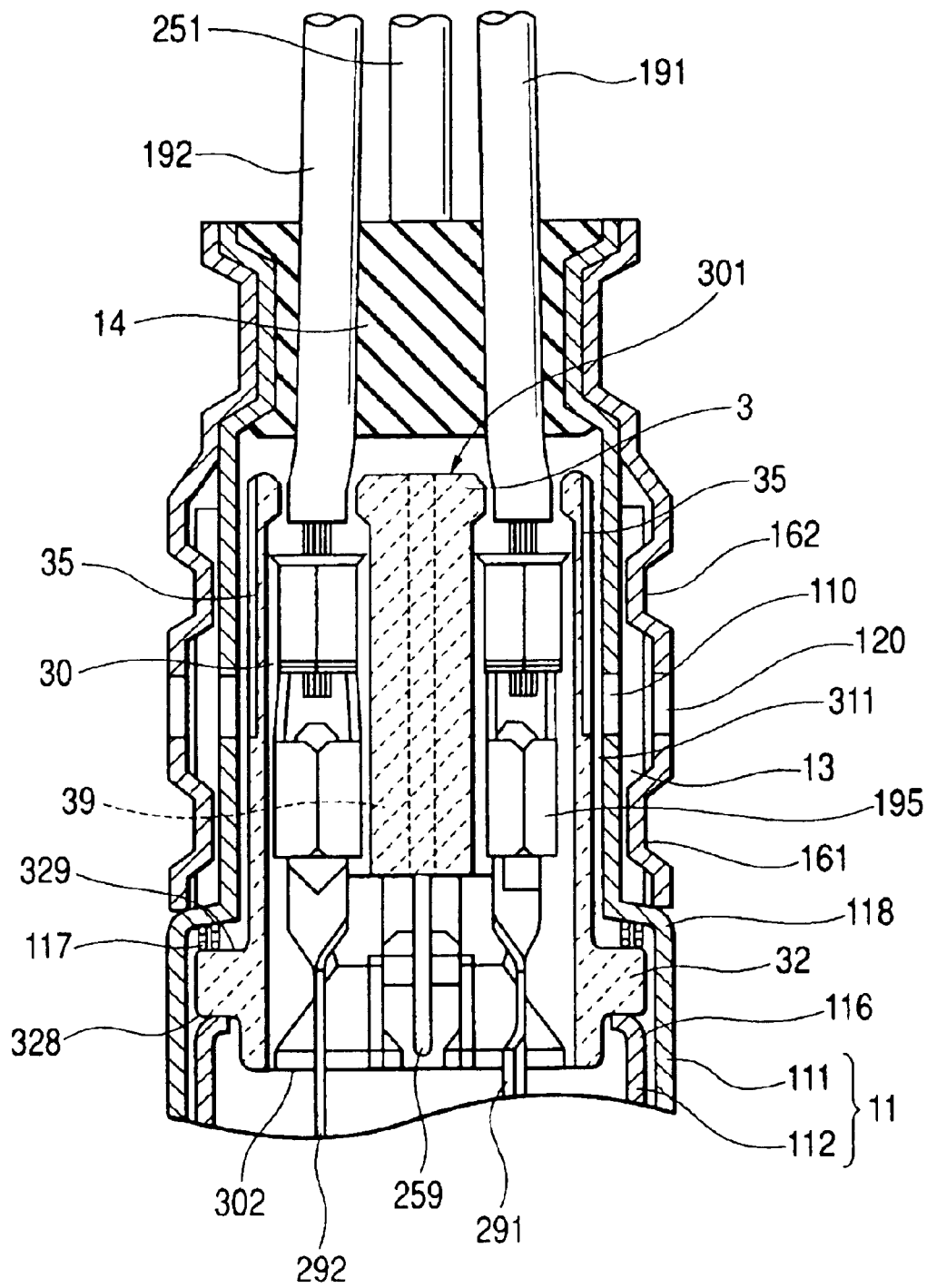
FIG. 2 is a partially enlarged view which shows a structure of an insulating holder of the first embodiment.

An insulating holder 3 is, as clearly shown in FIG. 2, disposed inside the first metallic cover 11 which has formed therein through holes 30 into which the leads 191 and 192 are inserted. The insulating holder 3 is made of a hollow cylindrical insulation porcelain and defines reference gas passages 35 between an outer wall 311 and an inner wall of the first metallic cover 11 which lead to the reference gas chamber 250.

The sensing unit 2 is, as shown in FIG. 1, retained within the housing 11. The sensing unit 2 and the housing 11 are hermetically sealed.

The first metallic cover 11 consists of two cover members: outer and inner cover members 111 and 112. The inner cover member 112 is joined at an end to an upper end of the housing 10 through a caulking ring 119. The outer cover member 111 is joined to an upper portion of the inner cover member 112 by crimping.

The inner cover member 112 has an open end 116, as shown in FIG. 2, abutting on a lower surface 328 of a large-diameter portion 32 (i.e., a flange) of the insulating holder 3 to retain the insulating holder 3 within the fist metallic cover 11 against a spring pressure of a spring 117 disposed between an upper surface 329 of the large-diameter portion 32 and a shoulder 118 of the outer cover member 111.

A sealing member 14 is fitted in an upper end of the inner cover member 112 through which the leads 191, 192, and 251 pass.

The insulating holder 3, as clearly shown in FIGS. 3(a) and 3(b), has formed therein four through holes 30 through which signal pickup leads 291 and 292, a pair of leads 259 connected to a heater 25, as will be described later in detail, the leads 191 and 192, and a pair of leads 251 pass. The leads 291, 292, and 259 are connected to the leads 191, 192, and 251 through connectors 195 within the through holes 30, respectively. Note that another pair of leads passes through the insulating holder 3, but it is located in an invisible area of the drawing and omitted here.

Figure 3A:
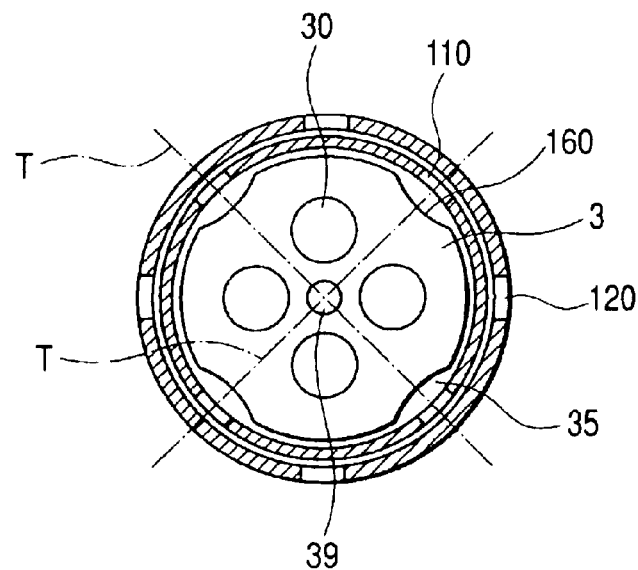
FIG. 3(a) is a horizontal sectional view taken along the line A—A in FIG. 3(b)
Figure 3B:
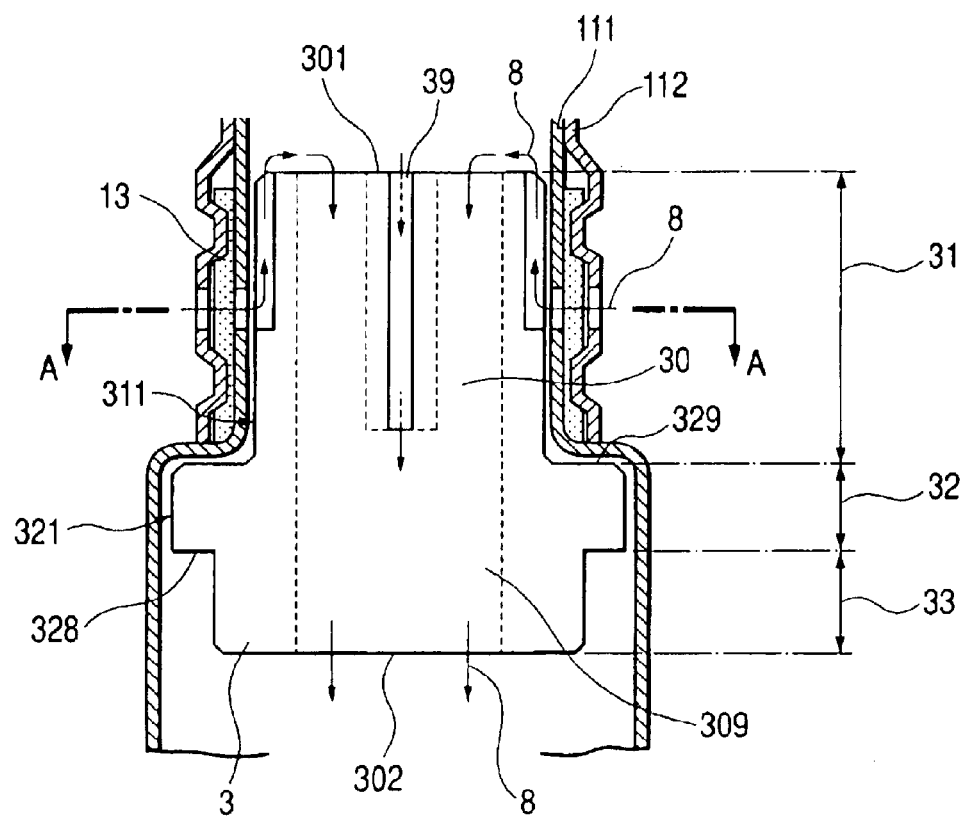
FIG. 3(b) is a longitudinal sectional view which shows reference gas passages defined in an insulating holder of the first embodiment.

The insulating holder 3 has formed in an a lower portion thereof, as shown in FIG. 3(b), a cavity 309 to which all the through holes 30 are exposed and in which a base portion of the sensing unit 2 is disposed.

Figure 4:
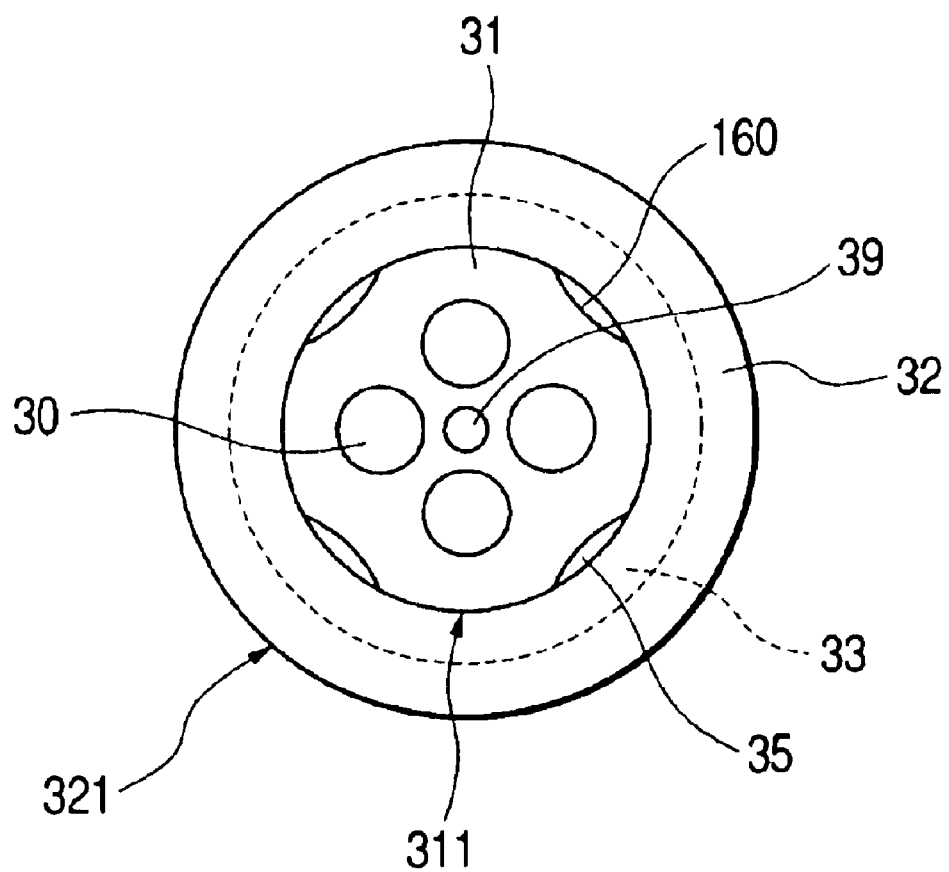
FIG. 4 is a horizontal sectional view which shows an insulating holder of the first embodiment.

The insulating holder 3, as shown in FIGS. 3(a) to 4, includes the large-diameter portion 32, a small-diameter portion 31, and a tip portion 33. The tip portion 33 projects from the large-diameter portion 32 toward the tip of the sensing unit 2 and is smaller in diameter than the large-diameter portion 32. These portions 31, 32, and 33 have circular sections, as clearly shown in FIG. 4. The large-diameter portion 32 and the small-diameter portion 31 are arranged coaxially, so that the interval between an outer wall 321 of the large-diameter portion 32 and an outer wall 311 of the small-diameter portion 31 is kept constant in a circumferential direction of the insulating holder 3. This eliminates the problem encountered in the prior art structure, as shown in FIGS. 21(a) and 21(b), that the insulating porcelain 9 is deformed during a production process.

The reference gas passages 35 are, as can be seen from FIGS. 3(a) and 4, defined between the inner wall of the outer cover member 111 and four grooves 160 provided in an outer wall 311 of the small-diameter portion 31 of the insulating holder 3. The grooves 160 each have an arc-shaped cross section and are, as shown in FIG. 3(a), formed at locations where lines T passing through the center of the insulating holder 3 between adjacent two of the through holes 30 intersect the outer wall 311 of the small-diameter portion 31. This allows the small-diameter portion 31 to have wider round outer surfaces formed at regular intervals in the circumferential direction of the insulating holder 3, thus resulting in an improved strength as compared with the prior art structure shown in FIGS. 21(a) and 21(b). Each of the reference gas passages 35 extends vertically, as viewed in FIG. 3(b), from one of the first air vents 110 to a base end 301 of the insulating holder 3.

The insulating holder 3 also has a central passage 39 extending along a longitudinal center line thereof which opens into the cavity 309.

The second metallic cover 12 is installed on the periphery of the upper portion of the first metallic cover 11 and is crimped to form, as shown in FIG. 2, two annular joints 161 and 162 to the first metallic cover 11 for retaining a water-repellent filter 13 between the first and second metallic covers 11 and 12. Specifically, the first metallic cover 11, the second metallic cover 12, and the water-repellent filter 13 are connected fixedly to each other through the annular joints 161 and 162.

The sensing unit 2, as shown in FIG. 1, consists of a hollow cylindrical solid electrolyte body 20 with a bottom, a measuring electrode formed on an outer wall of the body 20 exposed to a gas chamber 150, and a reference electrode formed on an inner wall of the body 20 exposed to the reference gas chamber 250. This structure is known, for example, in European Patent Application EP 0918215 A2 assigned to the same assignee as that of this application, disclosure of which is incorporated herein by reference.

Within the reference gas chamber 250, a bar-shaped heater 25 is disposed which heats the measuring and reference electrodes up to a temperature at which the oxygen concentration can be measured correctly. The measuring and reference electrodes have conductive terminals connected to the signal pickup leads 291 and 292. The heater 25 is supplied with power through the leads 259.

In operation, the air 8 which is, as indicated by arrows in FIG. 3(b), introduced from the second air vents 120 to the first air vents 110 through the water-repellent filter 13 flows upward, as viewed in the drawing, in the reference gas passages 35 and reaches the base end 301 of the insulating holder 3. Next, the air 8 passes through a gap between the base end 301 and the bottom of the sealing member 14 and flows downward into the cavity 309 through the holes 30 and the central holes 39. The air 8 emerging from the lower end 302 of the insulating holder 3 enters the reference gas chamber 250 at the upper end of the sensing unit 2.

The oxygen sensor 1 of this embodiment is designed to measure an oxygen content in gasses using the oxygen concentration dependent electromotive force or the limiting current. Specifically, the measurement of the oxygen content using the oxygen concentration dependent electromotive force is accomplished by monitoring through the measuring and reference electrodes the electromotive force produced in the solid electrolyte body 20 which depends upon a difference in oxygen concentration between the air 8 and the gas within the gas measuring chamber 150. The measurement of the oxygen content using the limiting current is accomplished by applying a given voltage across the measuring and reference electrodes to pick up a limiting current which depends upon the concentration of oxygen in the gasses. These techniques are known in the art, and explanation thereof in detail will be omitted here. The sensing unit 2 may alternatively be formed by laminations such as one shown in FIG. 5 in which the sensing unit 2 is made of a laminated plate having a heater layer. Further, U.S. Pat. No. 5,573,650, issued on Nov. 12, 1996 to Fukaya et al. teaches such a structure, disclosure of which is incorporated herein by reference.

Figure 6A:
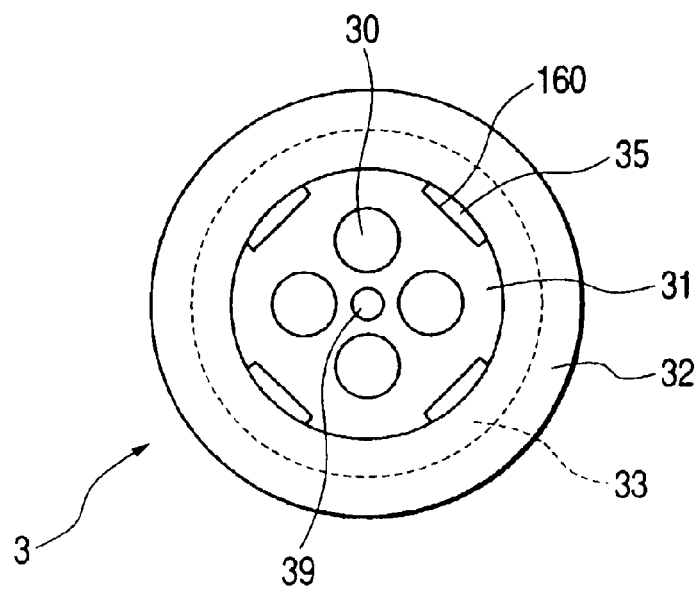
FIG. 6(a) is a lateral sectional view which shows a modification of the insulating holder of FIG. 4.
Figure 6B:
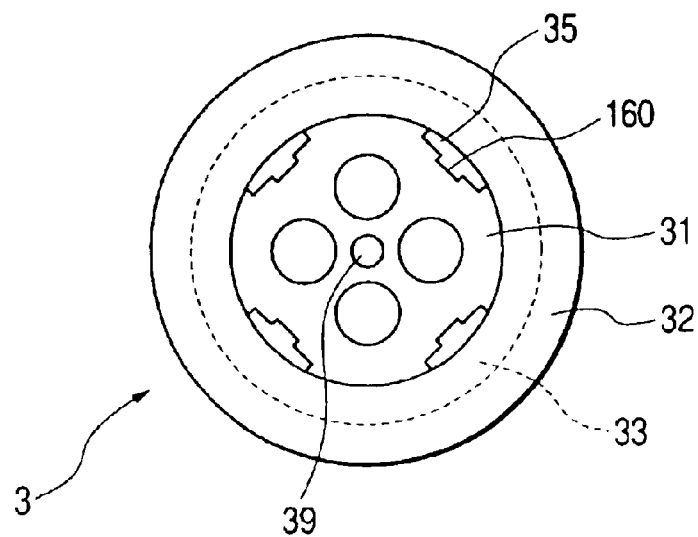
FIG. 6(b) is a lateral sectional view which shows another modification of the insulating holder of FIG. 4.

The grooves 160 formed in the small-diameter portion 31 of the insulating holder 3 to define the reference gas passages 35 may alternatively be of generally rectangular configuration in cross section, as shown in FIG. 6(a), or have parallel steps, as shown in FIG. 6(b), defining an additional central groove.

Figure 7:
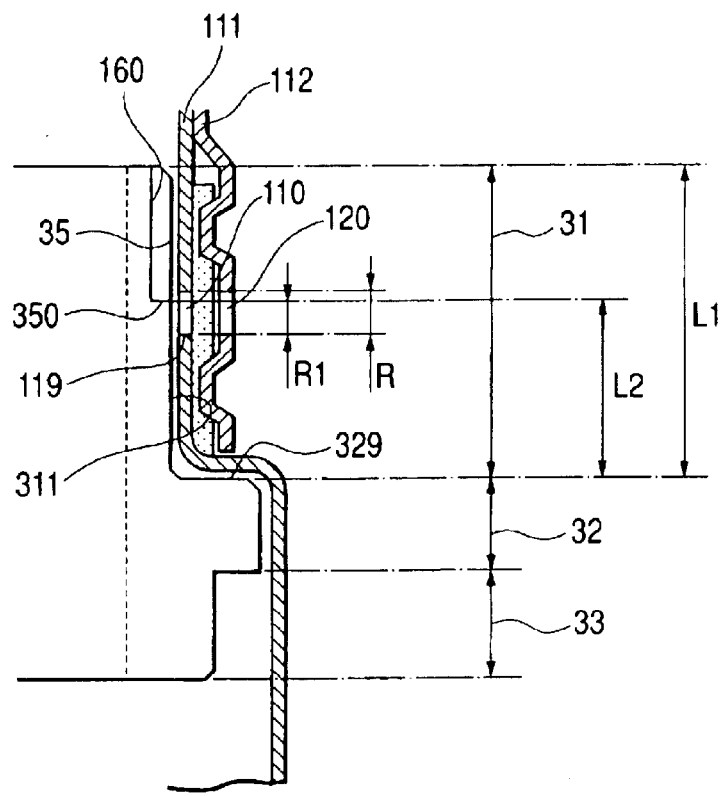
FIG. 7 is a partially vertical sectional view which shows reference gas passages of a gas sensor according to the second embodiment of the invention.

FIG. 7 shows the second embodiment of the invention.

The reference gas passages 35 are, like the first embodiment, defined by the grooves 160 formed in the outer wall 311 of the insulating holder 3, but each of the grooves 160 of this embodiment has a lower end 350 defining an inlet which leads to one of the first air vents 110 and which meets the following locational conditions.

Letting the length of the small-diameter portion 31 of the insulating holder 3 and the distance between the upper surface 329 of the large-diameter portion 32 and the lower end 350 of each of the grooves 160 be L1 and L2, respectively, L2 lies within a range of L1/5 to L1/2, preferably L1/3. For instance, L1=12.5 mm, and L2=6 mm. This allows the sensor to be decreased in size without sacrificing the strength of the small-diameter portion 31 of the insulating holder 3.

The lower ends 350 face the first air vents 110, respectively. If the diameter R of each of the first air vents 110 is defined as R, and the distance between a lowermost portion of 119 of each of the first air vents 110 and the lower end 350 of a corresponding one of the grooves 160 is defined as R1, then they are so selected as to meet a condition of R1≦R/3. For instance, R=2 mm, and R1 is 0.5 mm. This ensures the admission of a sufficient amount of air (i.e., the reference gas) into the sensor.

Other arrangements are identical with those in the first embodiment, and explanation thereof in detail will be omitted here.

Figure 8:
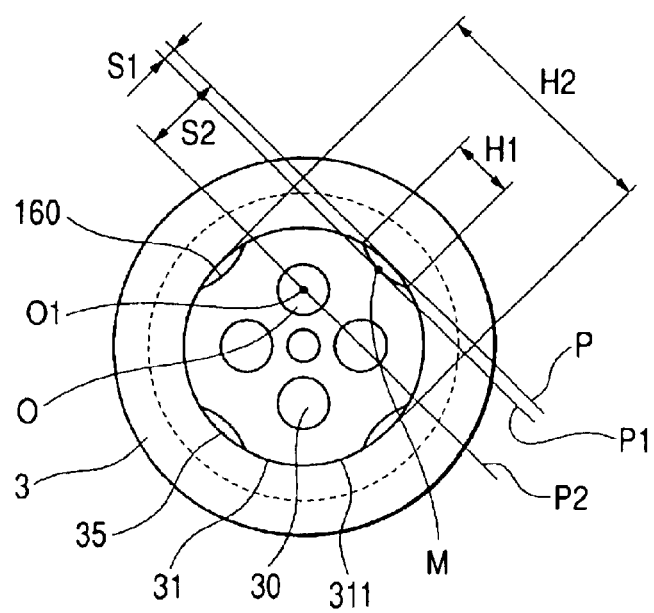
FIG. 8 is a lateral sectional view which shows reference gas passages of a gas sensor according to the third embodiment of the invention.

FIG. 8 shows the third embodiment of the invention.

The reference gas passages 35 are, like the first embodiment, defined by the grooves 160 formed in the outer wall 311 of the insulating holder 3, but the grooves of this embodiment 160 are designed so as to meet the following geometrically conditions.

If a plane tangent to the outer wall 311 of the small-diameter portion 31 is defines as P, a plane passing through the deepest point M of each of the grooves 160 in parallel to the plane P is defined as P1, and a plane passing in parallel to the plane P through the center O1 of one of the holes 30 located closest to the plane P is defined as P2, the distance S1 between the planes P and P1 is smaller than or equal to the distance S2 between the planes P and P2 (S1≦S2). For instance, S1=1 mm, and S2=2 mm.

If the width of each of the reference gas passages 35 is defined as H1, and the diameter of the small-diameter portion 31 of the insulating holder 3 is defined as H2, they are so selected as to meet a condition of $H1 \leq H2/2^{1/2}$, preferably H1≦(2×H2)/3. For instance, H1=3 mm, and H2=10 mm. Other arrangements are identical with those in the first embodiment, and explanation thereof in detail will be omitted here.

Figure 9:
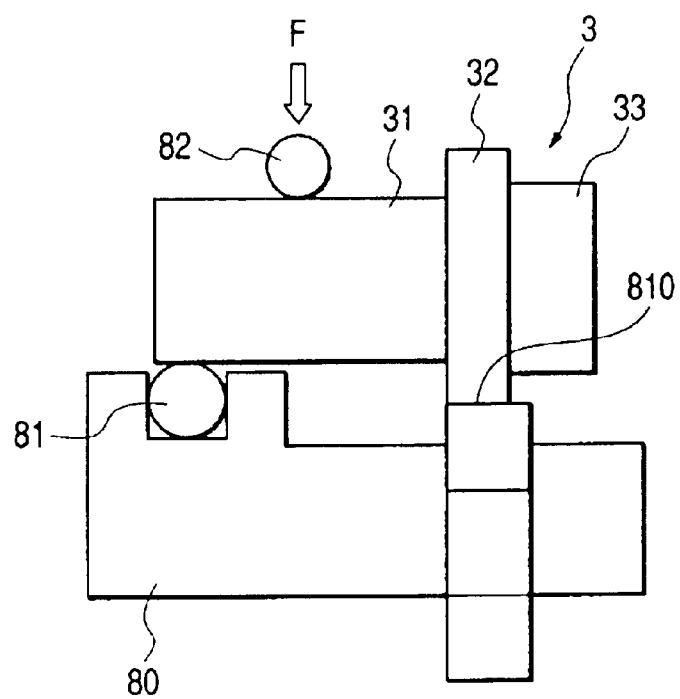
FIG. 9 shows a test machine used for measuring the strength of an insulating holder of the gas sensor in FIG. 8.

Strength tests were performed for a comparative test piece equivalent to the insulating holder 3 not having the grooves 60 in the small-diameter portion 31, the prior art insulation porcelain 9 shown in FIG. 21(a), and the insulating holder 3 of this embodiment using a test machine as shown in FIG. 9. The results of the tests are shown in FIG. 10.

The test machine has a table 80 on which a round bar 81 having a diameter of 5 mm is retained, and a support surface 810 is formed. The insulating holder 3 is placed in contact of the small-diameter portion 31 and the large-diameter portion 32 with the round bar 81 and the support surface 810, respectively. A round bar 82 having a diameter of 4 mm is placed on the small-diameter portion 31 of the insulating holder 3. The pressure F which causes the insulating holder 3 to be deformed 0.05 mm per minute is applied to the round bar 82 to measure the disruptive strength. The same texts were performed for the prior art insulation porcelain 9 and the comparative test piece.

Figure 10:
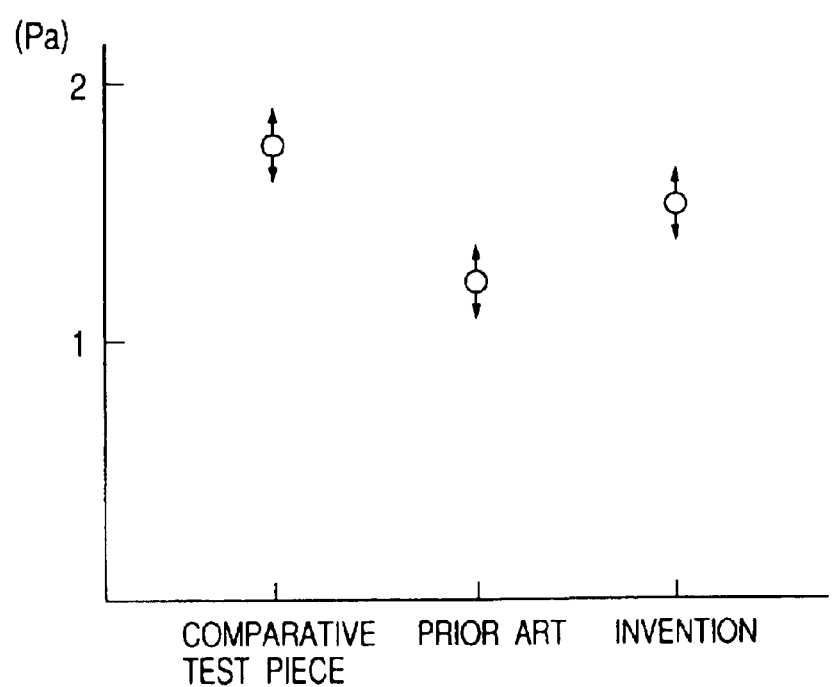
FIG. 10 is a graph which shows the strength of the insulating holder in FIG. 8.

The graph of FIG. 10 shows that the insulating holder 3 of this embodiment has a disruptive strength greater than that of the prior art insulation porcelain 9 closer to that of the comparative text piece.

Figure 11:
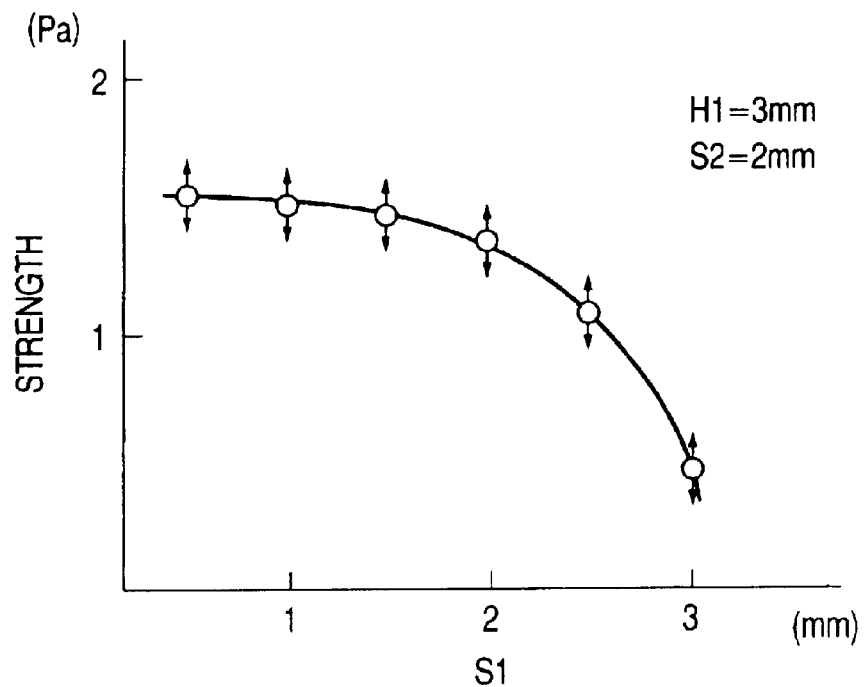
FIG. 11 is a graph which shows the strength of the insulating holder in FIG. 8 for different values of S1.

The strength texts were also performed on the insulating holders 3 in which H1=3 mm, S2=2 mm, and S1 has different values. The results of the tests are indicated in a graph of FIG. 11. As shown by the graph, the disruptive strength of the insulating holder 3 is decreased greatly when S1 exceeds S2(S1>S2).

Figure 12:
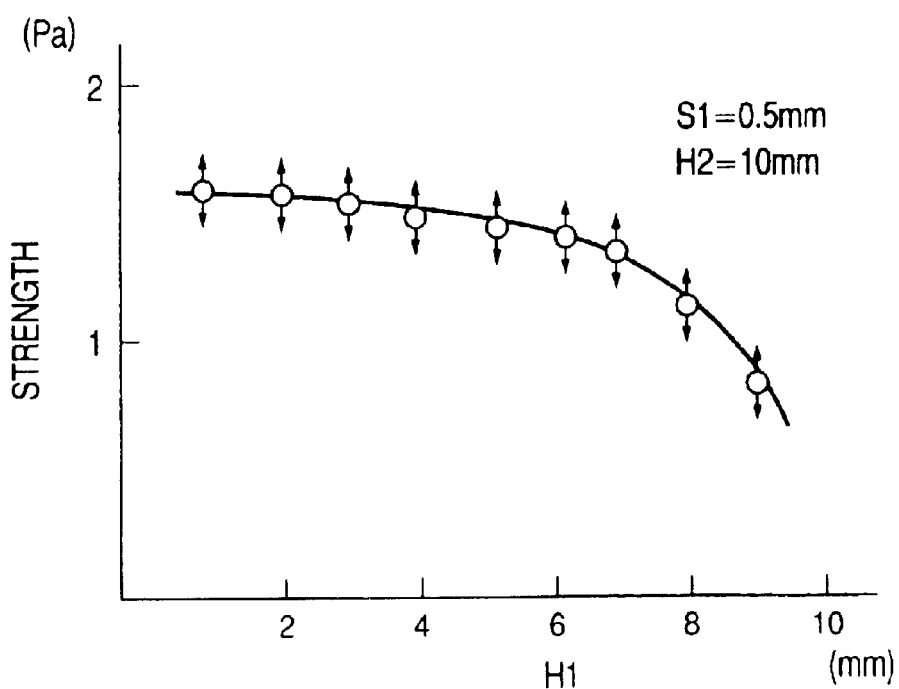
FIG. 12 is a graph which shows the strength of the insulating holder in FIG. 8 for different values of H1.

The strength texts were also performed on the insulating holders 3 in which S1=0.5 mm, H2=10 mm, and H1 has different values. The results of the tests are indicated in a graph of FIG. 12. As shown by the graph, the disruptive strength of the insulating holder 3 is decreased greatly when H1 exceeds $H2/2^{1/2}$.

Therefore, it is appreciated that the insulating holder 3 meeting the condition of S1≦S2 and/or the condition of $H1 \leq H2/2^{1/2}$ has an increased strength.

Figure 13A:
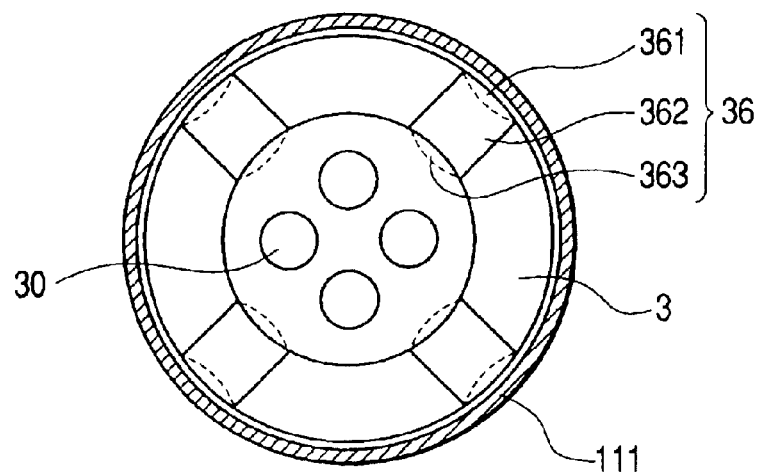
FIG. 13(a) is a horizontal sectional view taken along the line B—B in FIG. 13(b)
Figure 13B:
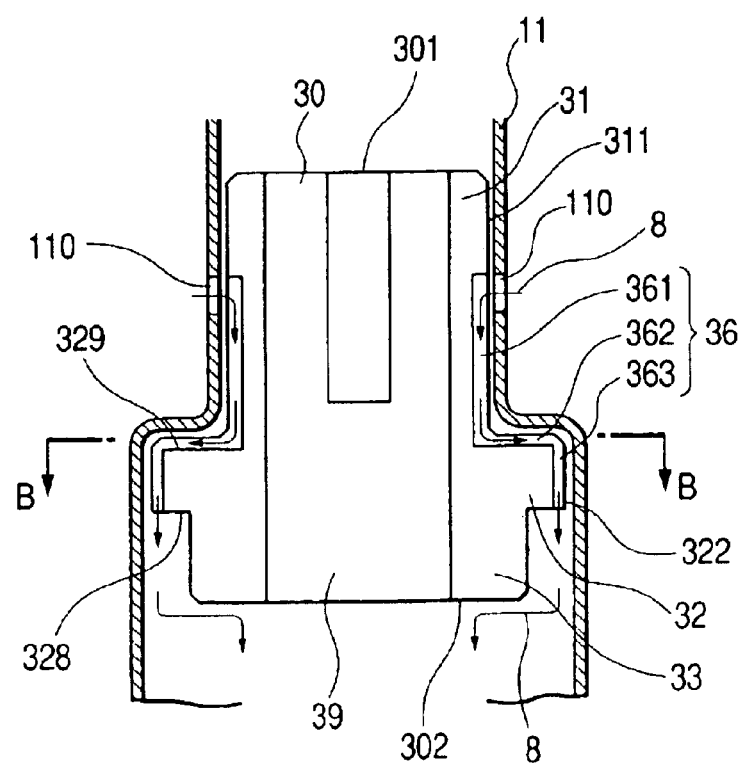
FIG. 13(b) is a longitudinal sectional view which shows reference gas passages defined in an insulating holder according to the fourth embodiment of the invention.

FIGS. 13(a) and 13(b) show the fourth embodiment of the insulating holder 3.

The insulating holder 3 has four grooves, similar in shape to the grooves 160 in the first embodiment, which are formed in the small-diameter portion 31 and the upper surface 329 and the side surface of the large-diameter portion 32 to define reference gas passages 36. Each of the grooves is made up of a vertical groove 361, a horizontal groove 362, and a vertical groove 363. The vertical grooves 361 are formed in the side wall of the small-diameter portion 31 at regular intervals. The horizontal grooves 362 formed in the upper surface 329 of the large-diameter portion 32. The vertical grooves 363 are formed in the side wall of the tip portion 33. Each of the reference gas passages 36 extends from one of the first air vents 110 to an annular gap defined between the tip portion 33 of the insulating holder 3 and the inner wall of the outer cover member 111. Other arrangements are identical with those in the first embodiment, and explanation thereof in detail will be omitted here.

Figure 14A:
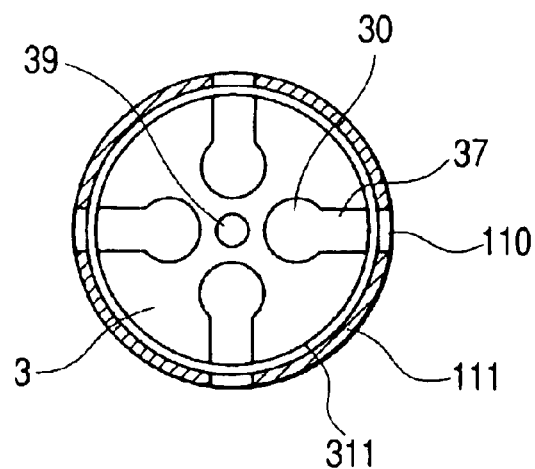
FIG. 14(a) is a horizontal sectional view taken along the line C—C in FIG. 14(b)
Figure 14B:
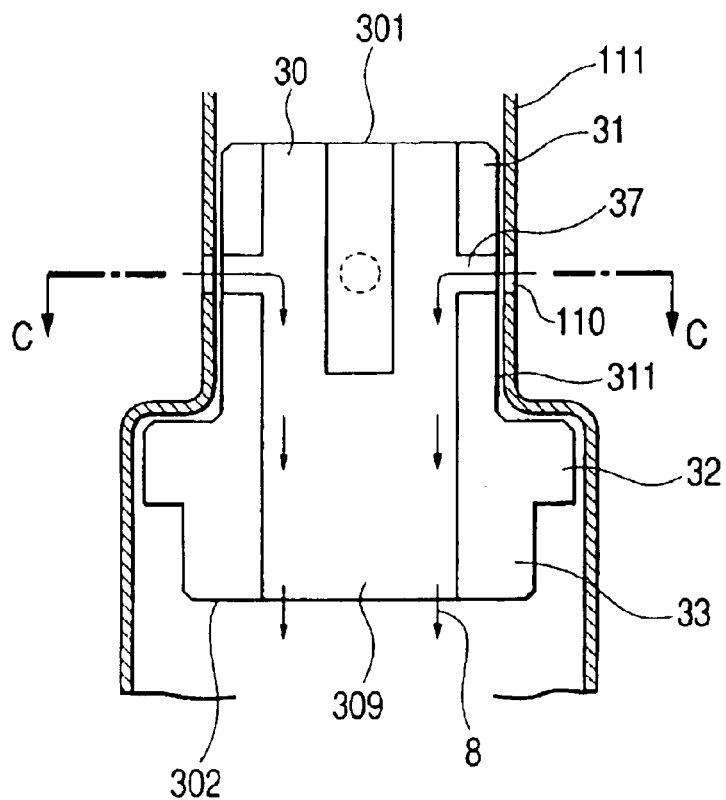
FIG. 14(b) is a longitudinal sectional view which shows reference gas passages defined in an insulating holder of the fifth embodiment.

FIGS. 14(a) and 14(b) show the fifth embodiment of the insulating holder 3.

The insulating holder 3 has four holes formed at regular intervals in the outer wall 311 thereof to define reference gas passages 37 extending horizontally, as viewed in FIG. 14(b). Each of the reference gas passages 37 establishes communication between one of the first air vents 110 and one of the through holes 30. Other arrangements are identical with those in the first embodiment, and explanation thereof in detail will be omitted here.

Figure 15A:
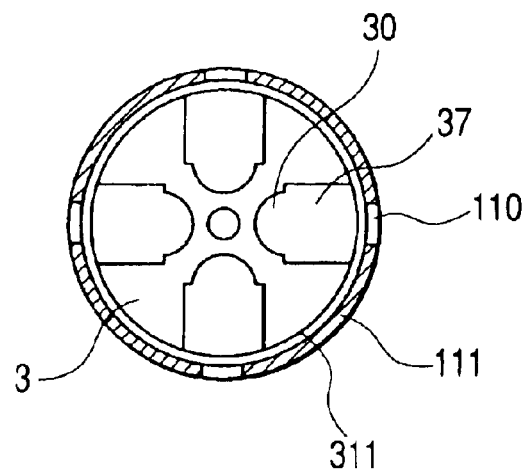
FIG. 15(a) is a horizontal sectional view taken along the line D—D in FIG. 15(b)
Figure 15B:
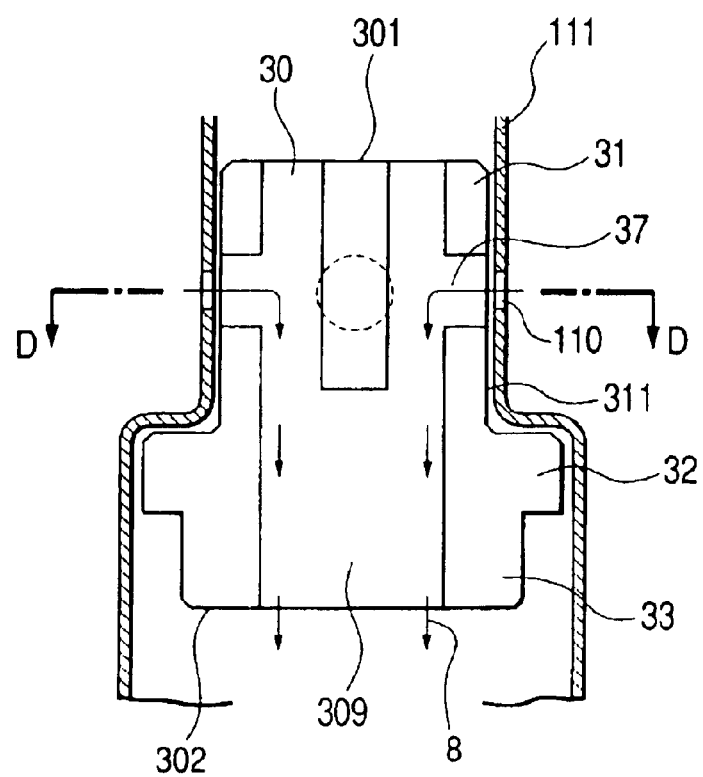
FIG. 15(b) is a longitudinal sectional view which shows reference gas passages defined in an insulating holder which is a modification of the one shown in FIGS. 14(a) and 14(b)

Four holes, as shown in FIGS. 15(a) and 15(b), which are greater in size than the through holes 30 may be formed at regular intervals in the outer wall 311 thereof to define the reference gas passages 37 extending horizontally, as viewed in FIG. 15(b).

FIG. 16 shows a modification of the fifth embodiment in FIGS. 14(a) and 14(b).

The insulating holder 3 has four holes defining reference gas passages 38. Each of the reference gas passages 38 extends from one of the air vent holes 110 to the central hole 39 between the adjacent two of the holes 30.

Each of the reference gas passages 37 and 38 in FIGS. 14(a), 14(b), 15(a), 15(b), and 16 may have any of different sectional shapes as shown in FIGS. 17(a), 17(b), and 17(c).

FIGS. 18(a) and 18(b) show the insulating holder 3 according to the sixth embodiment of the invention.

The insulating holder 3 has formed therein four vertical holes which define reference gas passages 41. Each of the reference gas passages 41 extends from one of the first air vents 110 to the cavity 309 in the insulating holder 3. Specifically, each of the reference gas passages 41 is made up of two sections: one is defined by a groove formed in the outer wall 311 extending from one of the first air vents 110 to a corner between the small-diameter portion 31 and the large-diameter portion 32 and the inner wall of the outer cover member 111 and the other is defined by a slant hole extending inwardly from the corner between the small-diameter portion 31 and the large-diameter portion 32 to the cavity 309. Other arrangements are identical with those in the first embodiment, and explanation thereof in detail will be omitted here.

FIGS. 19(a) and 19(b) show the insulating holder 3 according to the seventh embodiment of the invention.

The insulating holder 3 has an annular step 42 formed around the outer wall 311 of the small-diameter portion 31 to define an upper annular passage 170 and a lower annular passage 175 between the outer wall 311 and the inner wall of the outer cover member 111. Specifically, the upper annular passage 170 is greater in volume than the lower annular passage 175. The lower annular passage 175 directs the air 8 admitted from the first air vents 110 to the upper annular passage 170. The upper annular passage 170 directs the air 8 into the holes 30 and the central hole 39 through the base end 301 of the insulating holder 3. Other arrangements are identical with those in the first embodiment, and explanation thereof in detail will be omitted here.

FIG. 20 shows the insulating holder 3 according to the eighth embodiment of the invention.

The insulating holder 3 has a tapered wall 43 formed on the small-diameter portion 31 to define an annular passage 180 between itself and the inner wall of the outer cover member 111. The annular passage 180 increases in volume toward the base end 301 of the insulating holder 3 and directs the air admitted from the first air vents 110 into the holes 30 and the central hole 39 through the base end 301. Other arrangements are identical with those in the first embodiment, and explanation thereof in detail will be omitted here.

Figure 5:
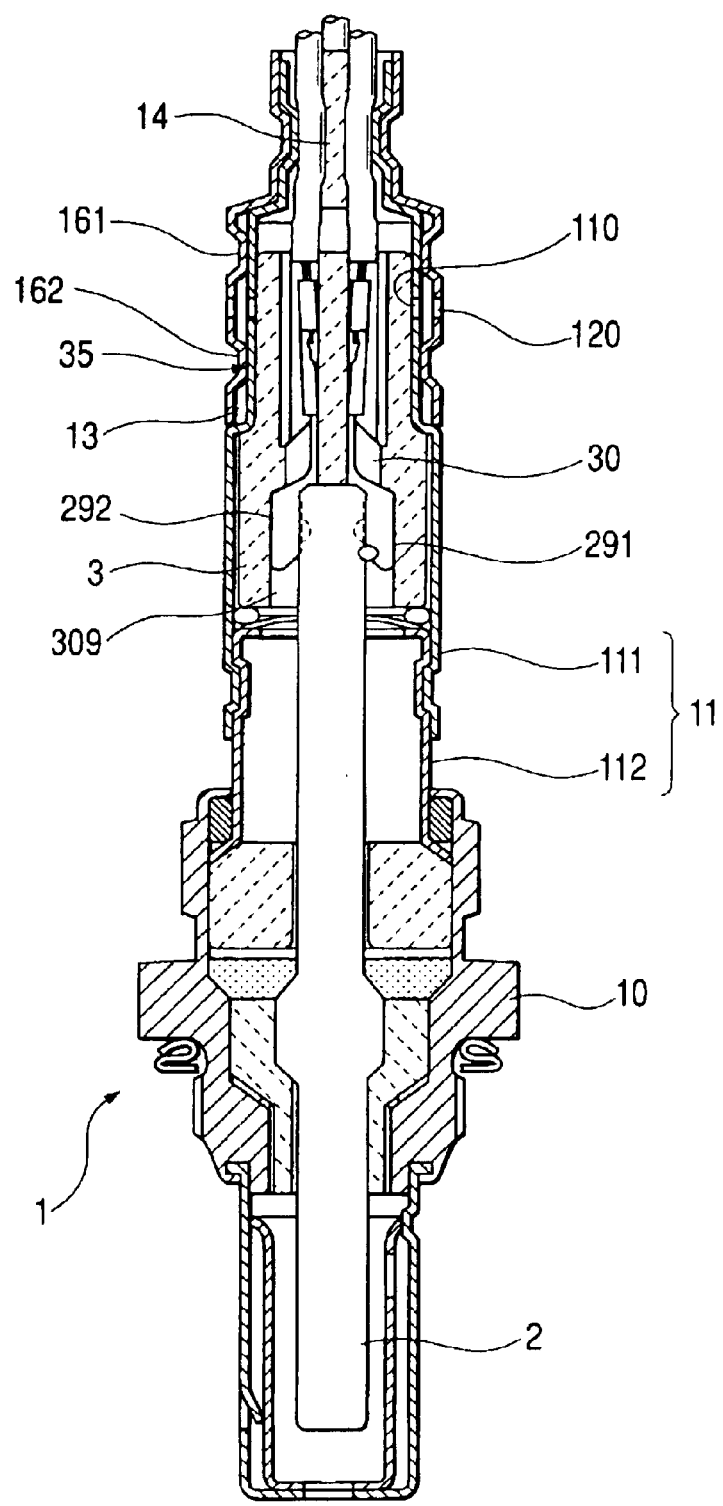
FIG. 5 is a longitudinal sectional view which shows another type of oxygen sensor equipped with an insulating holder in the first embodiment.

The above second to eighth embodiments may be used with the oxygen sensor shown in FIG. 1 or 5. Some of the first to eighth embodiments may be combined to form two or more types of reference gas passages in the insulating holder 3.

While the present invention has been disclosed in terms of the preferred embodiments in order to facilitate better understanding thereof, it should be appreciated that the invention can be embodied in various ways without departing from the principle of the invention. Therefore, the invention should be understood to include all possible embodiments and modifications to the shown embodiments witch can be embodied without departing from the principle of the invention as set forth in the appended claims.

What is claimed is:

1. A gas sensor measuring a given component content in a gas comprising:
    a housing;
    a sensing unit having a length disposed in said housing, said sensing unit having defined in a first end portion thereof a reference gas chamber to be filed with a reference gas used in providing a sensor signal through a lead which is employed in determining the given gas component content in the gas;
    a first metallic cover installed on said housing to cover a second end portion of said sensing unit;
    a second metallic cover installed on a periphery of said first metallic cover;
    a first vent formed in said first metallic cover;
    a second vent formed in said second metallic cover which communicates with said first vent to admit the reference gas into the reference gas chamber through a reference gas passage; and
    an insulating member disposed in said first metallic cover, having formed therein a hole through which the lead passes to connect with said sensing unit, said insulating member being made of a cylindrical porcelain having an outer peripheral wall which is substantially circular in cross section and which defines the reference gas passage,
    wherein said insulating member is arranged in alignment with said sensor unit and has a first end surface and a second end surface closer to said sensor unit said insulating member having a groove formed in the outer peripheral wall which extends from the first vent to the first end surface to define a portion of the reference gas passage and wherein the first vent has a diameter R in the longitudinal direction of the gas sensor, and a distance between a point on a periphery of the first vent closest to the second end surface of said insulating member and an upstream end of the groove facing the first vent is greater than or equal to R/3.

2. A gas sensor as set forth in claim 1, wherein said insulating member has a through hole extending in a direction of the first end surface to the second end surface to define a portion of the reference gas passage.

3. A gas sensor as set forth in claim 1, wherein said insulating member has a small-diameter portion formed closer to the first end surface and a large-diameter portion continuing from the small-diameter portion, and wherein if a length of the small-diameter portion in a direction is defined as L1, a distance L2 between the large-diameter portion and an upstream end of the groove facing the first vent lies within a range of L1/5 to L1/2.

4. A gas sensor as set forth in claim 1, wherein if a plane tangent to a periphery of said insulating member is defined as P, a plane passing through the deepest point of the groove in parallel to the plane P is defined as P1, and a plane passing in parallel to the plane P through the center of the through hole formed in said insulating member is defined as P2, a distance S1 between the planes P and P1 is smaller than or equal to a distance S2 between the planes P and P2.

5. A gas sensor as set forth in claim 1, wherein if a width of the reference gas passages defined on the outer peripheral wall of said insulating member is defined as H1, and a diameter of said insulating member is defined as H2, a condition of $H1 \leq H2/2^{1/2}$ is satisfied.

6. A gas sensor as set forth in claim 1, wherein said insulating member has formed therein a plurality of lead holes through which leads pass to connect with said sensing unit, and wherein the reference gas passage is defined at a location where a line passing through a center of said insulating member between adjacent two of the lead holes intersects the outer peripheral wall of said insulating member.

7. A gas sensor measuring a given component content in a gas comprising:
    a housing;

a sensing unit having a length disposed in said housing, said sensing unit having defined in a first end portion thereof a reference gas chamber to be filed with a reference gas used in providing a sensor signal through a lead which is employed in determining the given gas component content in the gas;

a first metallic cover installed on said housing to cover a second end portion of said sensing unit;

a second metallic cover installed on a periphery of said first metallic cover;

a first vent formed in said first metallic cover;

a second vent formed in said second metallic cover which communicates with said first vent to admit the reference gas into the reference gas chamber through a reference gas passage; and an insulating member disposed in said first metallic cover, having formed therein a hole through which the lead passes to connect with said sensing unit, said insulating member being made of a cylindrical porcelain having an outer peripheral wall which is substantially circular in cross section and which defines the reference gas passage, wherein said insulating member is arranged in alignment with said sensor unit and has a first end surface and a second end surface closer to said sensor unit, said insulating member having a groove formed in the outer peripheral wall which extends from the first vent to the second end surface to define a portion of the reference gas passage, and wherein if a plane tangent to a periphery of said insulating member is defined as P, a plane passing through the deepest point of the groove in parallel to the plane P is defined as P1, and a plane passing in parallel to the plane P through the center of the through hole formed in said insulating member is defined as P2, a distance S1 between the planes P and P1 is smaller than or equal to a distance S2 between the planes P and P2.

8. A gas sensor as set forth in claim 7, wherein said insulating member has a small-diameter portion formed closer to the first end surface and a large-diameter portion continuing from the small-diameter portion, and wherein if a length of the small-diameter portion in a direction is defined as L1, a distance L2 between the large-diameter portion and an upstream end of the groove facing the first vent lies within a range of L1/5 to L1/2.

9. A gas sensor as set forth in claim 7, wherein if a width of the reference gas passages defined on the outer peripheral wall of said insulating member is defined as H1, and a diameter of said insulating member is defined as H2, a condition of $H1 \leq H2/2^{1/2}$ is satisfied.

10. A gas sensor as set forth in claim 7, wherein said insulating member has formed therein a plurality of lead holes through which leads pass to connect with said sensing unit, and wherein the reference gas passage is defined at a location where a line passing through a center of said insulating member between adjacent two of the lead holes intersects the outer peripheral wall of said insulating member.

* * * * *